(12) United States Patent
Binmoeller

(10) Patent No.: US 8,034,063 B2
(45) Date of Patent: Oct. 11, 2011

(54) METHODS AND SYSTEMS FOR TREATING HIATAL HERNIAS

(75) Inventor: Kenneth F. Binmoeller, Rancho Santa Fe, CA (US)

(73) Assignee: XLumena, Inc., Mountain View, CA (US)

( * ) Notice: Subject to any disclaimer, the term of this patent is extended or adjusted under 35 U.S.C. 154(b) by 378 days.

(21) Appl. No.: 12/172,967

(22) Filed: Jul. 14, 2008

(65) Prior Publication Data
US 2009/0018576 A1    Jan. 15, 2009

Related U.S. Application Data

(60) Provisional application No. 60/949,746, filed on Jul. 13, 2007.

(51) Int. Cl.
| | |
|---|---|
| A61B 17/08 | (2006.01) |
| A61F 2/00 | (2006.01) |
| A61F 13/00 | (2006.01) |
| A61F 2/04 | (2006.01) |
| A61F 2/02 | (2006.01) |

(52) U.S. Cl. ..... 606/151; 600/37; 623/23.64; 623/23.72
(58) Field of Classification Search ................... 606/151, 606/153, 139; 623/23.72, 23.64, 23.7, 23.74; 600/37
See application file for complete search history.

(56) References Cited

U.S. PATENT DOCUMENTS

| | | |
|---|---|---|
| 5,081,993 A | 1/1992 | Kitney et al. |
| 5,993,393 A | 11/1999 | Ryan et al. |
| 6,773,441 B1 | 8/2004 | Laufer |
| 6,821,285 B2 | 11/2004 | Laufer |
| 6,835,200 B2 | 12/2004 | Laufer |
| 6,960,233 B1 * | 11/2005 | Berg et al. ..................... 623/23.7 |
| 7,120,498 B2 | 10/2006 | Imran |
| 7,153,314 B2 | 12/2006 | Laufer |
| 7,232,445 B2 | 6/2007 | Kortenbach |
| 7,267,694 B2 * | 9/2007 | Levine et al. ................. 623/23.7 |
| 2004/0193184 A1 * | 9/2004 | Laufer et al. .................. 606/139 |
| 2005/0033328 A1 * | 2/2005 | Laufer et al. .................. 606/153 |
| 2005/0228415 A1 * | 10/2005 | Gertner ......................... 606/153 |
| 2005/0277957 A1 * | 12/2005 | Kuhns et al. .................. 606/148 |
| 2006/0015125 A1 | 1/2006 | Swain |
| 2006/0025819 A1 * | 2/2006 | Nobis et al. ................... 606/232 |
| 2006/0282087 A1 * | 12/2006 | Binmoeller .................... 606/139 |
| 2007/0038232 A1 * | 2/2007 | Kraemer ........................ 606/153 |
| 2007/0088373 A1 | 4/2007 | Baker |
| 2007/0112363 A1 | 5/2007 | Adams |
| 2007/0129738 A1 | 6/2007 | Kraemer |
| 2007/0135825 A1 * | 6/2007 | Binmoeller .................... 606/153 |
| 2007/0142884 A1 | 6/2007 | Jandrall |

* cited by examiner

Primary Examiner — Darwin Erezo
Assistant Examiner — Dianne Dornbusch
(74) Attorney, Agent, or Firm — Wilson Sonsini Goodrich & Rosati

(57) ABSTRACT

The present invention relates generally to medical methods and systems used to restore the angle of His and treat hiatal hernias and other conditions of the lower esophagus. More particularly, the present invention relates to a method and system that allows fixation of the distal esophagus and fundus of the stomach directly to the diaphragmatic crus muscle. The present invention provides a method where the diaphragmatic crus muscle is identified and precisely located from within and through the gastrointestinal lumen followed by the placement of a translumenal anchor which connects and secures the esophagus and stomach to the diaphragmatic crus muscle. This procedure reduces the hiatal hernia, restores the normal anatomy and treats conditions associated with the lower esophagus.

30 Claims, 18 Drawing Sheets

METHODS AND SYSTEMS FOR TREATING HIATAL HERNIAS

CROSS-REFERENCE TO RELATED APPLICATIONS

The present application claims the benefit of U.S. Provisional Patent Application No. 60/949,746, filed on Jul. 13, 2007, under 37 C.F.R. §1.78, the complete disclosure of which is incorporated herein by reference for all purposes.

BACKGROUND OF THE INVENTION

1. Field of Invention

The present invention relates generally to medical methods and apparatus. More particularly, the present invention relates to a method and system for restoring the angle of His and treating and stabilizing hiatal hernias.

Hiatal hernias (also referred to as a hiatus hernia) result when the diaphragm muscle, in particular the diaphragmatic crus, loosens and can no longer firmly hold the esophagus and stomach in their normal position. The esophagus and stomach are able to move in the cranial direction resulting in the stomach being herniated above the diaphragm and into the thoracic cavity. When the hiatal hernia occurs, the esophagus and fundus move upward creating an obtuse angle which facilitates recurrent reflux. The correct configuration at the angle of His is an acute angle which prevents reflux. Hiatal hernias also reposition the lower esophageal sphincter (LES) away from the diaphragmatic crus muscle resulting in a weakening of this structure. Further decrease in LES tone and a shortened LES segment is more likely to result in acid reflux.

A common complication and symptom of hiatal hernia is gastroesophageal reflux disease (GERD). Reflux occurs when the gastroesophageal valve does not close tightly enough or relaxes at the wrong time. Gastroesophageal reflux disease, commonly known as heartburn, acid stomach, or reflux esophagitis, is a common disorder that affects people worldwide. More than 40% of Americans experience typical heartburn on a regular basis, and 10% suffer from heartburn at least once per day. Acid suppressive medication may address occasional or minor GERD; however, reflux often persists despite drug therapy.

Gastroesophageal reflux disease that is untreated over a long period of time can lead to complications, such as esophageal ulcers or perforations. Another common complication is scar tissue that blocks the movement of swallowed food and drink through the esophagus. This condition is called esophageal stricture. Esophageal reflux may also cause less common symptoms, such as hoarseness or chronic cough, and sometimes provokes conditions such as asthma. Overall, at least 19 million American adults experience GERD, making it one of the most common medical conditions. Chronic or severe GERD may cause esophagitis, esophageal stricture and/or Barrett's esophagus.

Medication, open surgical procedures and endoscopic techniques are known for treating GERD. Additionally, and of particular interest to the present invention, a variety of minimally invasive protocols have been developed to treat reflux disease. For example, methods have been developed for creating plications (i.e. folds or tucks) using tissue fasteners in the cardia of the stomach to form a flap of tissue that acts as an anti-reflux valve.

Current minimally invasive treatment protocols suffer from at least three shortcomings. First, creating tissue plications in the cardia of the stomach does not necessarily result in proper reconfiguration of the angle of His or the lower esophageal sphincter which prevents regurgitation of the stomach contents into the esophagus. Second, these plications do not secure the esophagus or stomach or significantly reduce the hiatal hernia. Third, attachment of the tissue fasteners to the tissue of the stomach are unstable and tend to migrate.

For these reasons, it is desirable to provide improved methods and systems for restoring the angle of His and treating hiatal hernias and other conditions by attaching a portion of the lower esophageal wall to the fundus of the stomach and the diaphragmatic crus muscle.

2. Background Art

Minimally invasive methods for treating GERD and related conditions are described, for example, in U.S. Pat. Nos. 7,153,314, 6,835,200, 6,821,285 and 6,773,441 as well as U.S. Patent Application Publication Nos. 2007/0129738, 2007/0112363 and 2007/0088373. Additional U.S. Pat. Nos. 7,232,445, 7,120,498, and U.S. Patent Application Publication Nos. 2007/0142884, 2007/0038232, 2006/0282087, 2006/0015125 and 2005/0277957. Methods to identify internal structures via ultrasound are described in U.S. Pat. Nos. 5,081,993 and 5,993,393, for example.

BRIEF SUMMARY OF THE INVENTION

The present invention provides improved methods and systems for restoring the angle of His and treating hiatal hernias and other conditions of the lower esophagus. While the methods will be suitable for treating patients with GERD, they will be more broadly applicable to patients having or at risk from suffering from hiatal hernias, even if no symptoms of GERD are present. The present invention provides a method for placing and positioning an anchor which connects and secures the esophagus and stomach to the diaphragmatic crus muscle. In order to assure the proper reconfiguration of the angle of His and the reliable capture of the crus muscle, the presence of the crus muscle between the esophagus and stomach is confirmed prior to the placement of the anchor. This restores the native, normal anatomy and thereby treats and reduces the hiatal hernia.

A first method according to the present invention comprises moving the hiatal hernia downwardly to capture a crus muscle between a wall of the lower esophagus and a gastric fundus. The crus muscle is an outgrowth of the diaphragm which attaches in two portions to each of the lumbar vertebrae. Confirming the location of the crus muscle may be accomplished by visualizing it using ultrasonic imaging or by a number of other methods further described below. Because the crus muscle cannot be seen visually from the inside of the gastrointestinal lumen, endoesophageal endoscopic visualization is not sufficient and it is usually necessary to ultrasonic image or other imaging or non-imaging techniques to locate the crus muscle prior to deploying the fastener. Also, the stomach and esophagus are not always fixed, especially in the case of a sliding hiatal hernia, and the structures can move relative to one another and out of alignment as in the normal non-herniated anatomy. Correctly identifying and targeting the location of the crus is also important since there are many vital organs in the vicinity which can be accidentally perforated or injured leading to serious complications. These organs include, but are not limited to, the aorta, kidney, liver and pancreas.

In one embodiment, at least the lower esophageal wall is fastened to the gastric fundus with a fastener that passes through the crus muscle at a target site when the position of the crus muscle between the fundus and esophageal wall has been confirmed. To move the hiatal hernia, an instrument, such as an endoscope, is advanced down the esophagus. The end of the instrument is engaged against the herniated portion of the esophageal wall. The hernia is then pushed toward the stomach and the position of the crus muscle confirmed.

After the hiatal hernia or other tissue deformity has been reconfigured and the location of the crus muscle has been identified, the lower esophageal wall and the fundus are attached with a fastener that passes through the crus muscle. This is accomplished by deploying a delivery device and advancing the fastener through the delivery device. Fastening can occur in the direction from the esophagus toward the fundus. Alternatively, fastening can occur in the direction from the fundus toward the esophagus. By passing the fastener through the crus muscle, any tendency for the fastener to migrate is limited or eliminated and the resulting attachment is stabilized. The fastener comprises a central portion having two expandable end anchors which expand and engage the esophagus and fundus, respectively.

Further advantages of this method include a fastener that is stretchable, flexible, removable and adaptable to movement and variations in anatomy. The procedure can be performed by a gastroenterologist rather than surgeons, takes less time than conventional surgery, has fewer complications and side-effects and has lower overall procedural costs than conventional methods. The procedure recreates or augments the natural anatomy.

A second method according to the present invention comprises restoring the angle of His by positioning an instrument in the esophagus, confirming a crus muscle is captured between the lower esophageal wall and the gastric fundus and fastening the lower esophageal wall to the gastric fundus with a fastener that passes through the diaphragmatic crus muscle. In particular aspects of the present invention, an instrument, such as a conventional endoscope or, preferably, and EUS endoscope, is positioned in the esophagus of a patient. The cuff or other inflatable member on the endoscope may be inflated to engage the tissue of the hernia. By pushing downwardly, the hiatal hernia is stretched and the esophagus and fundus are repositioned allowing the angle of His to be restored to it's natural configuration.

The fastener is advanced through a delivery device and passes from the thoracic cavity to the abdominal cavity. Fastening restores the gastrointestinal flap valve, repositions the lower esophageal sphincter against the diaphragmatic crus muscle, enhances the function of the lower esophageal sphincter, and restores the anti-reflux barrier. The angle of His is restored by treating the hiatal hernia.

A third method according to the present invention comprises treating a hiatal hernia by fastening the lower esophageal wall to the gastric fundus with a fastener that passes through the diaphragmatic crus muscle. The hiatal hernia is first pushed or pulled downwardly to capture the crus muscle at the angle of His. This results in reducing the hernia. Pushing or pushing the hiatal hernia comprises engaging the hernia with the expanded cuff of the endoscope (or other device) and pushing the hernia downward. The hernia can be pushed or pulled down by mechanical pushers, vacuum apparatus, inflatable members, pins, traction devices or the like, either associated with an endoscope or as separate devices. The fastener is advanced through the endoscope and delivered using a catheter to pass the fastener from the thoracic cavity to the abdominal cavity since it passes from the superior to inferior surface of the diaphragmatic crus. Fastening restores the gastro-esophageal flap valve, repositions the lower esophageal sphincter against the crus muscle, enhances the function of the lower esophageal sphincter and restores the anti-reflux barrier. The angle of His is restored by treating the hiatal hernia.

The fastener has a central portion and two expandable end anchors which expand and engage the esophagus and gastric fundus, respectively. The anchors may be self-expanding so that as they are advanced through the tissue and released, the distal end will expand adjacent to the inner wall of the fundus, and the proximal end will expand adjacent to the inner wall of the esophagus. Optionally, the fasteners may include a means for drawing the two end anchors together to tighten or cinch the fastener.

These and other features, aspects and advantages of the present invention will become better understood with regard to the follow description, appended claims and accompanying drawings.

DETAILED DESCRIPTION OF THE INVENTION

The medical methods and systems described herein offer improvements over the techniques currently utilized to perform endoscopic procedures to reduce hiatal hernias, restore the angle of His and to treat other conditions of the lower esophagus. The present invention relates to novel methods and systems that fix the distal esophagus and fundus directly to the diaphragmatic crus muscle. The present invention provides several embodiments where the crus is precisely identified followed by the placement of a translumenal anchor which connects, fastens and secures the esophagus and/or stomach to the diaphragmatic crus. This procedure reduces the hiatal hernia and restores the anatomy to its normal configuration.

Figure 1:
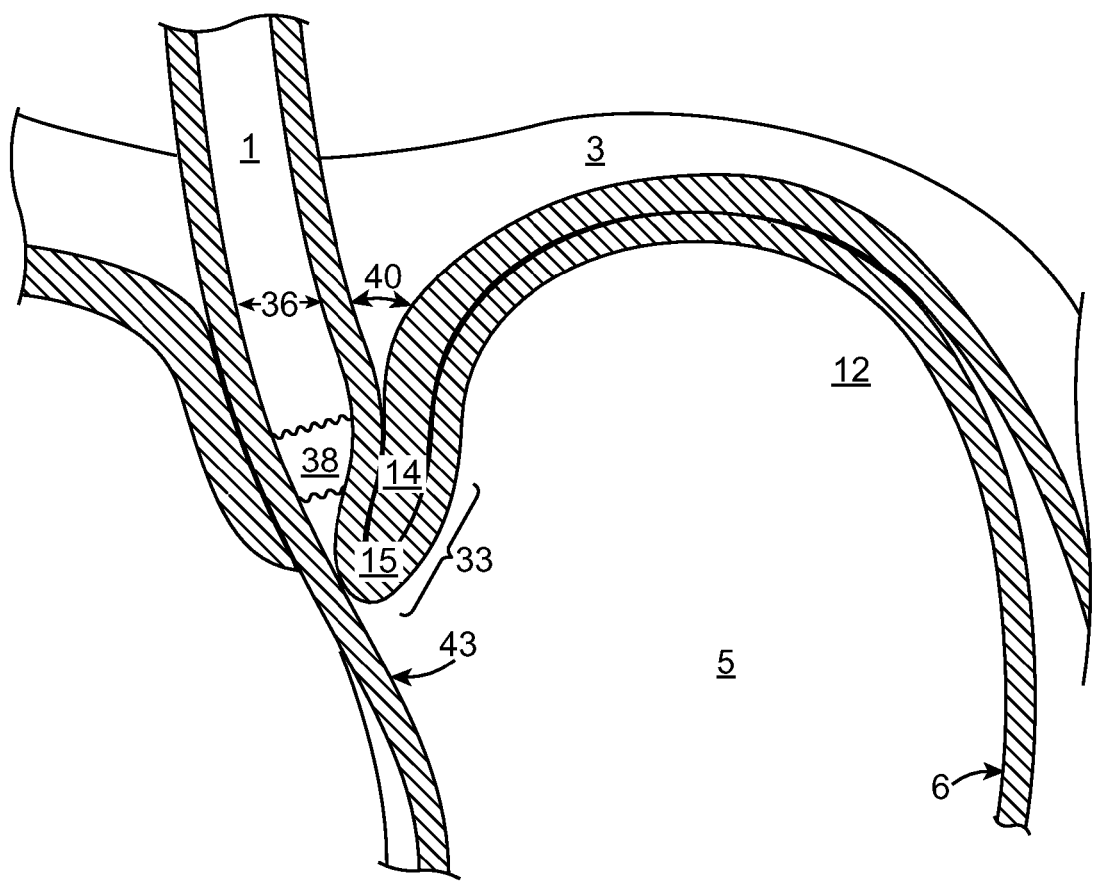
FIG. 1 is a cross sectional view of the gastrointestinal tract in the area of the gastroesophageal junction (GEJ) depicting a normal anatomy.

FIG. 1 is a cross sectional view of the gastrointestinal tract in the area of the gastroesophageal junction (GEJ), from the esophagus 1 to the stomach 5 depicting a healthy anatomy, including a normal gastro-esophageal valve (GEV) 33 with correct angle of His 15 and crus muscle 14 location. In this state, the top of the fundus of the stomach 12 is superior to the location where the esophagus empties into the stomach. The fundus 12 forms the superior portion of the stomach 5. The esophagus 1 enters the stomach 5 at a point below the top of the fundus 12 forming the cardiac notch 40 and an acute angle with respect to the fundus 12 at the angle of His 15. The lower esophageal sphincter (LES) 38 is an important primary sphincter that controls the movement of fluids and food into the stomach. In the closed configuration the GEV 33 rests securely on the adjacent lesser curve of the stomach 43. The GEV is formed from three structures: the distal esophagus, the diaphragmatic curs and the wall of the fundus. This flap is several centimeters long and it is partially held against the opposing wall of the stomach 5 by the internal pressures of the stomach. The esophageal tract is primarily controlled by the LES 38 and the GEV 33. The LES 38 is located just superior to the angle of His 15. The GEV 33 prevents stomach acids and other substances from moving back into the esophagus. Although, the LES 38 and the GEV 33 work together to prevent reflux of stomach contents into the esophagus, it is the GEV that is of primary importance. Failure or misalignment of these structures, including the failure to close properly can cause GERD.

Figure 2:
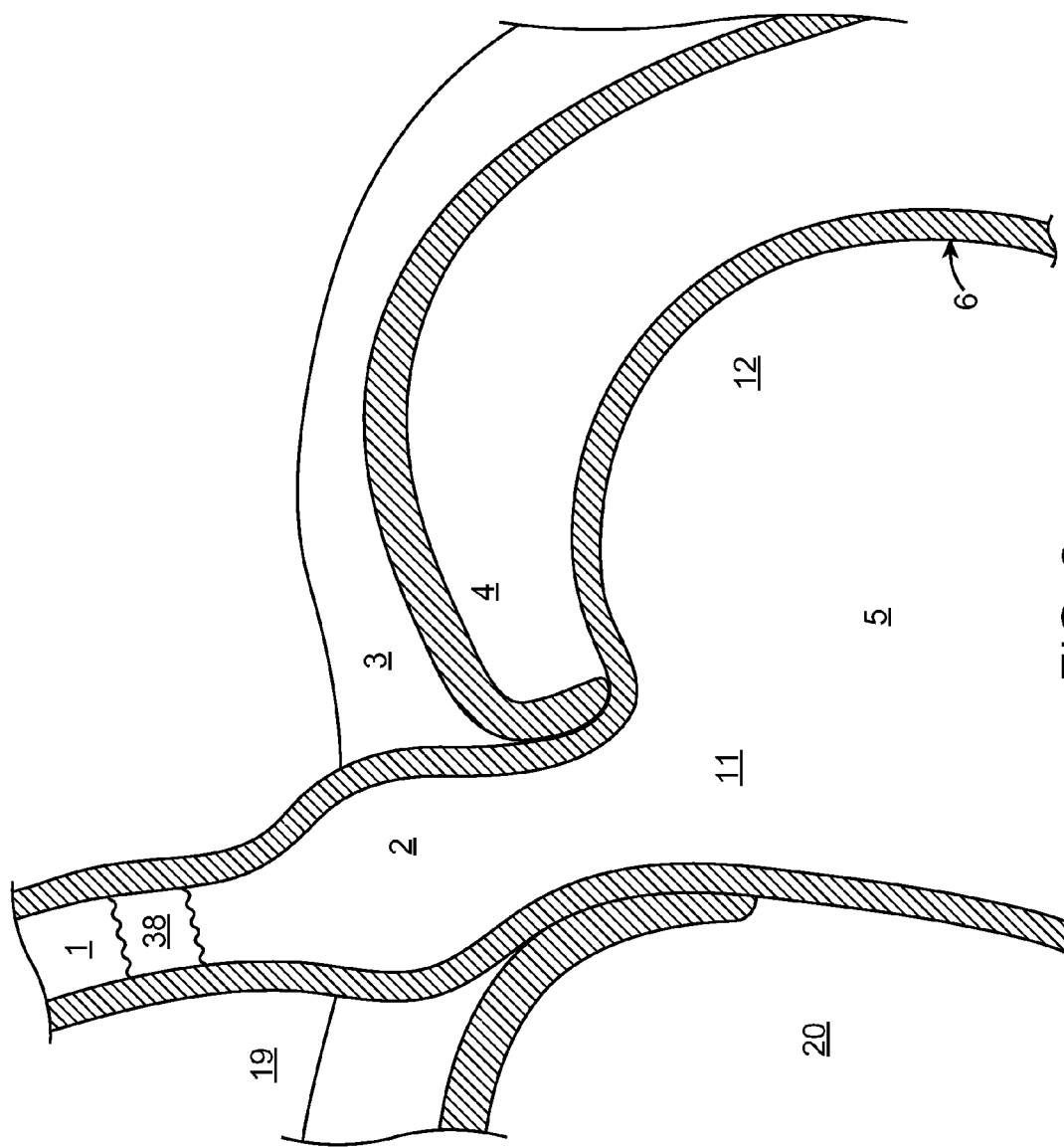
FIG. 2 is a cross sectional view of the gastrointestinal tract in the area of the gastroesophageal junction (GEJ) depicting a hiatal hernia formed over the diaphragm.

FIG. 2 is a cross sectional view of the gastrointestinal tract depicting a disease state in the area of the GEJ. Specifically, FIG. 2 shows a sliding hiatal hernia 2 formed over the diaphragm 3. As a result of the sliding hernia, the GEV and angle of His are anatomically absent, which often leads to illnesses including conditions such as GERD. In the herniated state, the fundus of the stomach 12 moves in the caudal direction away from the underside of the diaphragm and to a position that can be inferior to the position of where the esophagus empties into the stomach. The lower esophageal sphincter, 38 moves in a cranial direction and is often superior to the diaphragmatic cura. FIG. 2 also depicts a misalignment of the GEJ at the angle of His and the absence of the GEV.

Figure 3:
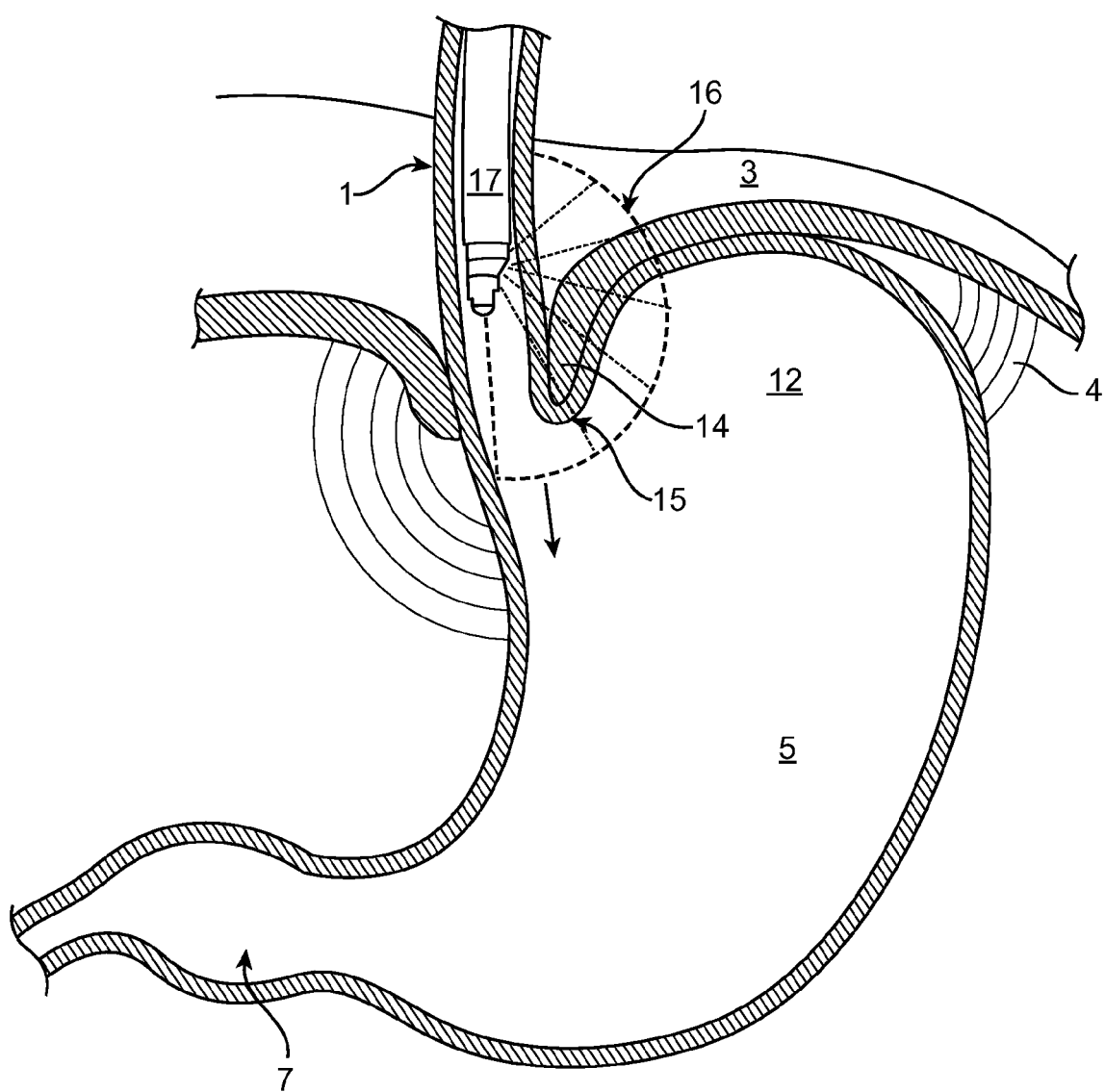
FIG. 3 is a cross sectional view of the gastrointestinal tract in the area of the gastroesophageal junction (GEJ) depicting a normal anatomy illustrating the use of a transoral side viewing echo-endoscope positioned in the distal esophagus and facing toward the fundus of the stomach.

FIG. 3 is a cross sectional view of the gastrointestinal tract in the area of the GEJ with an instrument 17, preferably an endoscopic ultrasound (EUS) endoscope, inserted through the oral cavity (not shown) and downward into the distal esophagus 1. A gastroenterologist or other health care professional manipulates the EUS endoscope down the esophagus of a patient. In a preferred embodiment, ultrasound can be used to visualize tissues and organs outside the gastrointestinal lumen. Of particular interest of the present invention is to visualize and identify anatomical structures (or confirm the lack thereof) near and around the diaphragm 3 with particular attention to the crus, 14 located in the direction of the fundus 12. One example of the EUS viewing plane 16 is shown in FIG. 3.

During transoral endoscopy of a patient with a sliding hernia, the friction of the endoscope often pushes the esophagus downward, with concurrent movement of the fundus upward to a normal position, making endoscopic visualization of the hernia difficult. Hiatal hernias are often difficult to detect using standard visual endoscopy. This is because these hernias are most often "sliding". This means that the stomach can prolapse above the diaphragm into the herniated position (about 1 to 4 cm) and then return to a normal configuration. In the patient with a sliding hernia, the anatomy alternates from the normal to herniated configuration through the course of the day. It is common; therefore, that endoscopy underestimates the presence and extent of a hernia. However, careful insertion of the endoscope to minimize friction, combined with minimal insufflation of air, can allow positioning of the scope without significant reduction of the hernia. Once the scope is in the stomach, the hernia can be visualized by retroflexing the scope to visualize the fundus and GEJ. The visual observation of the depth of the fundus and anatomical configuration at the GEJ is sufficient to categorize a hiatal hernia.

Figure 4:
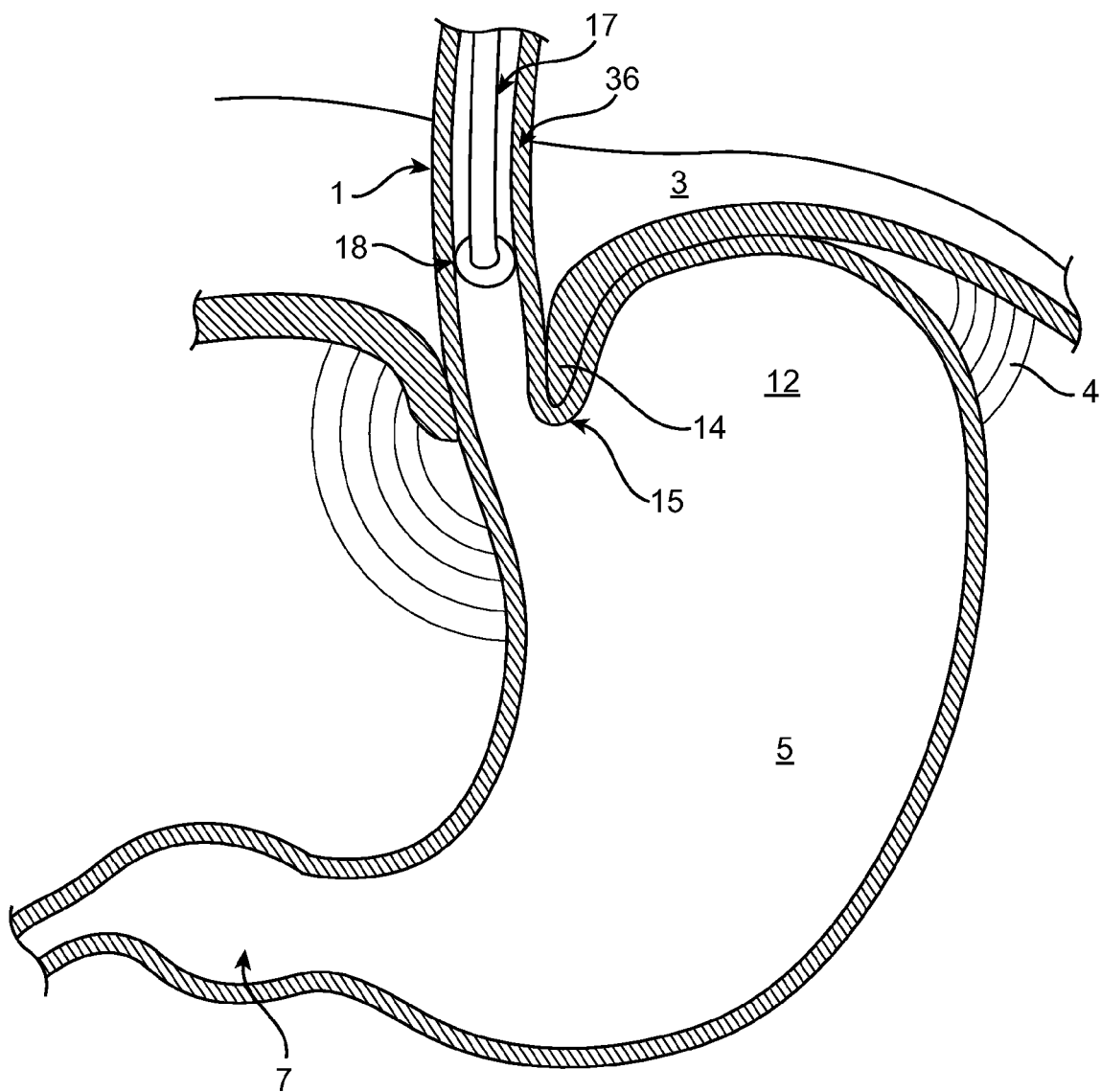
FIG. 4 is a cross sectional view of the esophageal-gastrointestinal tract illustrating the use of an endoscope with inflatable member deployed to engage the esophageal wall and reconfigure the angle of His.

If the movement of the scope downward does not reduce the hernia, it is possible to move the esophagus downward, with concurrent movement of the fundus upward, through the use of an inflatable member 18 as seen in FIG. 4. A grasper, vacuum cap or other such device that can be deployed to engage the esophageal wall 36 and press, knead, massage or otherwise push or pull the hiatal hernia 2 in an caudal direction below the diaphragm 3 to a normal anatomical configuration can also be used. Engaging the esophageal wall and pulling downward on the esophagus reduces the hernia and reconfigures the angle of His 15 so that the crus muscle 14 is captured between the lower wall of the esophagus 36 and the fundus 12.

Figure 12:
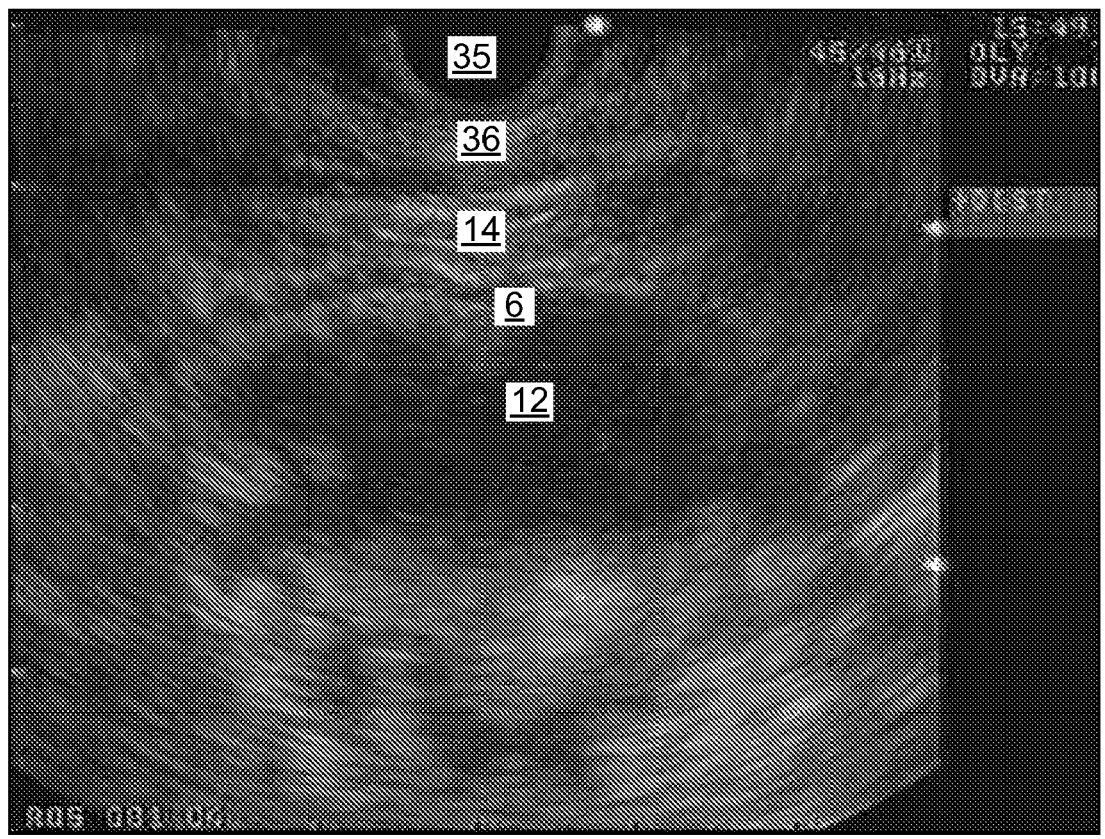
FIG. 12 is a view of a linear endoscopic ultrasound image of the crus muscle and other anatomical landmarks.

In a preferred embodiment the location of the crus is confirmed using an EUS endoscope 17. For example, FIG. 12 is an ultrasonic image from a linear EUS endoscope of the anatomy at and around the GEJ. The upper center dark semicircle is the EUS transducer 35 and the origin of the ultrasound signal. Presenting below the transducer are a number of key anatomical structures that are both internal and external to the gastrointestinal lumen, including the wall of the esophagus 36, the crus muscle 14 (external to the gastrointestinal lumen) the wall of the fundus 6, the fundus cavity 12 (internal to the gastrointestinal lumen) and surrounding anatomy.

Figure 13:
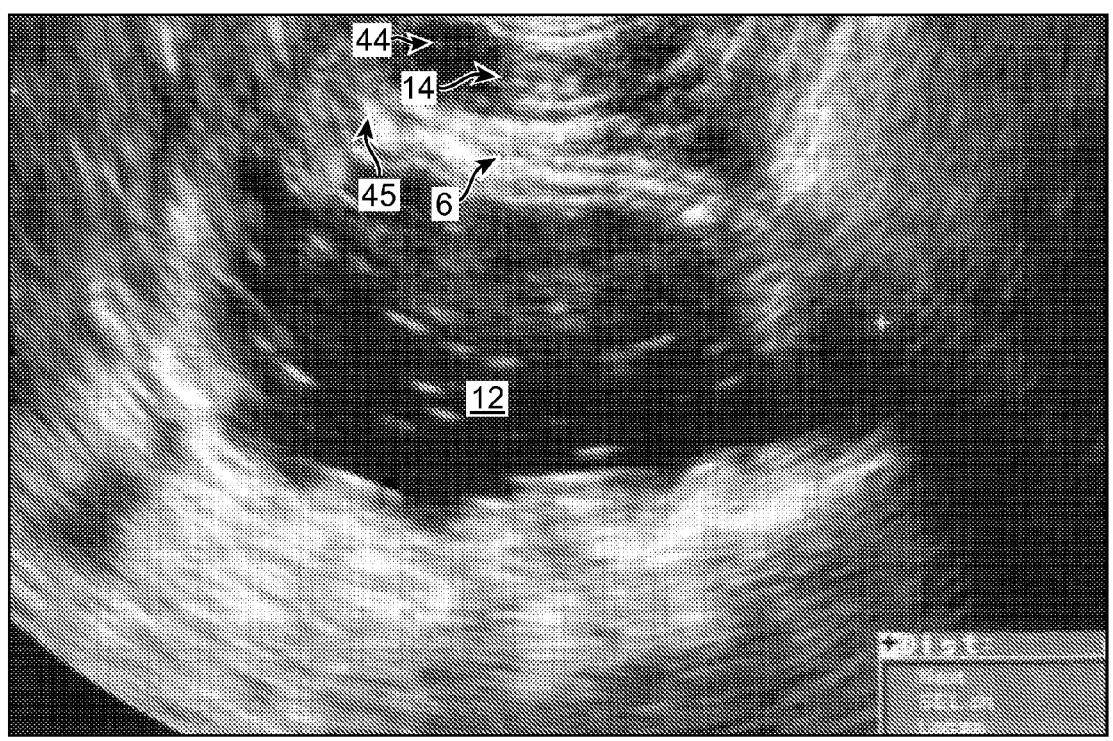
FIG. 13 is a view of a linear endoscopic ultrasound image showing normal anatomy with a crus muscle that is aligned with the angle of His.

EUS can also be used to detect and categorize a hernia. For example, FIG. 13 is an image from a linear EUS endoscope in the area of the GEJ, similar to that seen in FIG. 12, and specifically showing normal anatomy: the inferior edge 44 of crus muscle 14 and the inferior edge 45 of the wall of the fundus (stomach 6) at the GEJ and the angle of His. Of particular interest is the alignment of the lower edge of the crus 44 with the lower edge of the fundus 45 at the angle of His. Alignment of these structures represents a normal non-herniated anatomy.

Figure 14:
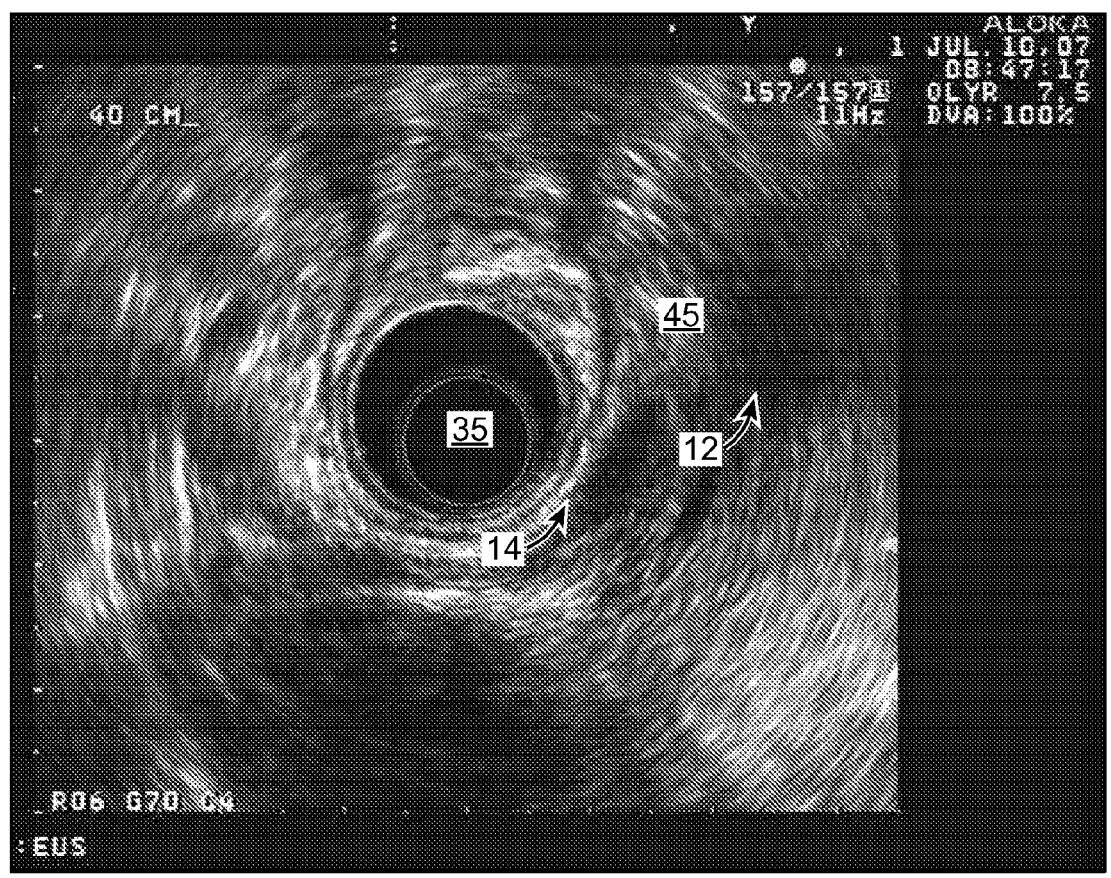
FIG. 14 is a view of a radial endoscopic ultrasound image showing normal anatomy in a patient without a hiatal hernia.

A radial EUS endoscope can also be used to detect and categorize a hernia. FIG. 14 is an image of a non-herniated patient from a radial EUS endoscope. The EUS endoscope transducer 35 is inserted approximately 40 cm into the distal esophagus, typically showing the crus muscle 14 aligned with the GEJ. In a herniated patient, the crus will remain at about 40 cm, while the GEJ will be located upward at a distance less than 40 cm. This is diagnostic of a hiatal hernia.

An alternative means to endoscopically diagnose a hernia is to identify the level of the diaphragmatic "pinch" caused by the crus muscle wrapping around distal esophagus at the GEJ using direct visual techniques. In the normal non-herniated anatomy the diaphragmatic "pinch" will be aligned to within 1 cm of the GEJ. In the anatomy with a hiatal hernia the discrepancy in alignment of the diaphragmatic "pinch" and the GEJ will be greater than about 1 cm.

Numerous other methods can be used to directly or indirectly visualize, palpate, or otherwise identify the presence and/or location of the diaphragm and/or crus muscle. Therefore, prior to deploying the translumenal anchor or any other method of attachment, confirmation that the crus is in its normal location and configuration (i.e. sandwiched between the esophagus and fundus at the angle of His) can be accomplished by employing one, or any combination, of the following examples: 1) ultrasound from within the GI lumen or outside the GI lumen as part of an endoscope or part of another device or as a single device; 2) Magnetic Resonance Imaging (MRI); 3) CT scanning; 4) fluorography with markers or contrast agents; 5) nuclear imaging with tagged cells; 6) spectroscopy using techniques such as either infrared or Raman; 7) palpation and/or visualization around the angel of His with or without the use of a standard visual endoscope; 8) cautiously probing through the GI lumen, esophageal wall or wall of the fundus; 9) carefully palpating the GI lumen, esophageal wall, or wall of the fundus; 10) taking a biopsy sample of the crus; 11) laparoscopic or open surgery; and 12) impedance sampling to differentiate crus from GI lumen wall tissue.

The following is one example of an alternative embodiment including procedural protocols for employing a radioisotope or magnetic tag (i.e. iron) or any other label that produces a signal alone or in conjunction with another imaging methodology that is detectable through the wall of the esophagus or fundus of from any location within the GI tract, body cavity or external to the body that indicates the presence of the crus muscle: 1) administer patient IV with anti-human muscle tag followed by saline drip for about 3-6 hours to allow background signal to be removed from the blood stream; 2) position a trans-oral detector facing to the left of the patient at the distal esophagus; 3) detect the signal from the tag in the area around the GEJ; 4) note the presence of signal above a threshold at the angle of His. The location of this signal indicates the presence of the crus muscle.

In yet another alternative embodiment, the anti-human muscle antibody can be tagged with a fluoroscopic contrast agent and fluorography can be used to identify the location of the crus muscle.

Prophetic methods to visualize the crus muscle may include, but are not limited to, the use of Electrical Impedance Tomography (3D EIT) and Positron Emission Tomography (PET). Impedance Tomography is an imaging modality that recovers the spatial variation of the complex impedivity in the body from electrical measurements made on the periphery. PET scans produce images of the body functions unobtainable by other imaging techniques.

While PET scans (and MRI), for example, today cannot be done during the procedures described herein (i.e. in real time), they can be completed immediately before the procedures and, with adequate resolution, these scans can confirm the presence of the crus between the distal esophagus and fundus. The procedure described herein could then be completed essentially immediately after the scan is completed, provided the patient is relatively immobile throughout the scan and procedure.

Impedance can also be used to verify presence of the crus muscle. A very small probe (in the form of a needle or trocar) can be placed across the esophageal wall, external to the gastrointestinal lumen. Tissue impedance monitoring can be initiated, such that a signal is emitted to the user when the electrically conductive probe has penetrated into diaphragmatic crus or stomach wall tissue. Since these tissues have different electrical conductivity properties, small pulses of electrical signals will conduct differently depending on the tissue the probe has been placed within. The electrical signal required to generate impedance values in tissue would be minimal and brief, such that no other tissue effect would be imparted.

In addition to the methods described above, many other endoluminal, translumenal or external (to the body) methods to image or identify the presence and/or location of the diaphragm or crus can also be used. Whatever method is chosen to identify the crus muscle, it's also very important to locate other vital structures including, but not limited to, veins and arteries, and organs such as the heart, kidney, liver and pancreas to ensure they are not engaged during the procedure or otherwise injured.

After the hernia has been resolved, usually accomplished by passing the EUS endoscope down the esophagus of the patient, and locating the crus muscle identified between the esophageal wall 36 and fundus wall 6 at the angle of His 15, a fastener is delivered to the target site through a delivery device 26 that is deployed from the EUS endoscope 17 in a direction toward the fundus (FIGS. 5-10).

Figure 11A:
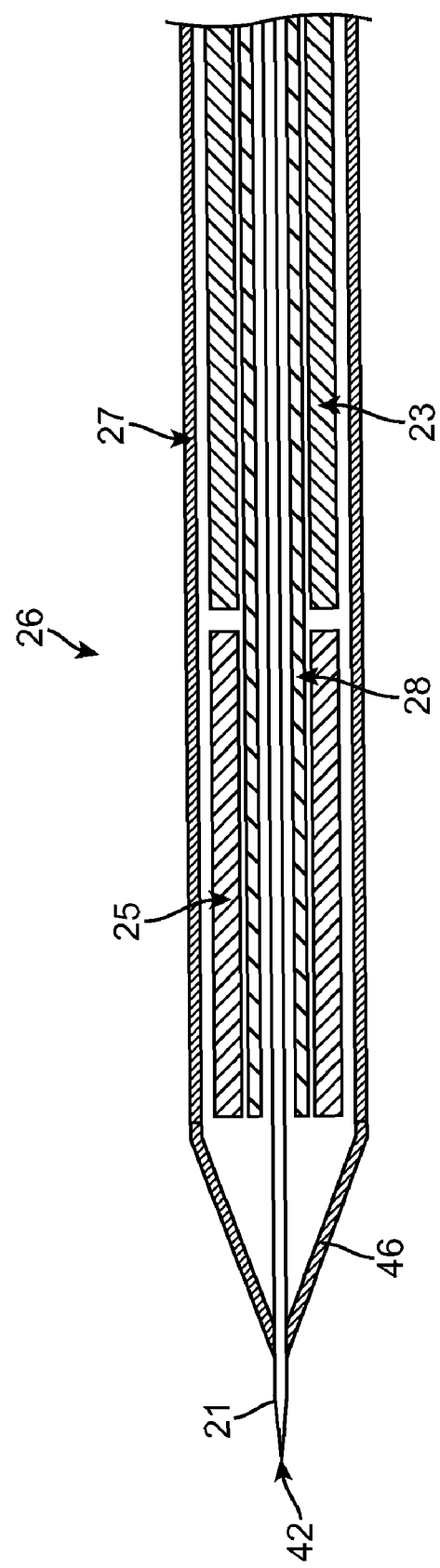
FIG. 11A is a perspective view of the distal end of an exemplary delivery device including a delivery catheter with nose cone, an anchor with pusher catheter, a guiding catheter and a needle or trocar.

In a preferred embodiment, FIG. 11A shows a cross sectional view of an exemplary device. The delivery device 26 consists of an outer delivery catheter 27, a constrained anchor 25 with pusher catheter 23, inner guiding catheter 28 with tapered nose cone 46 and a hollow needle or solid trocar 21 with sharp tip 42. The needle 21 is sized to fit through the inner guiding catheter 28 and the anchor is designed to fit closely over the inner guiding catheter 28 and inside the delivery catheter 27. The entire delivery device 26, including the outer delivery catheter, anchor, pusher catheter, inner guiding catheter and needle are designed to fit through an endoscope working channel. The size of a standard endoscopic working channel ranges from about 1.5 mm to about 6 mm, more commonly 2 mm to 5 mm, depending on the endoscope, although this system may function equally well with larger diametric requirements. The size of the delivery needle 21 is preferably 14 to 26 gauge, and more preferably, 19 to 22 gauge.

The proximal end of the delivery needle 21 may include a handle (not shown) which can be secured to the inlet port of the endoscope working channel by a luer lock mechanism, for example. Each part of the delivery device is designed to be advanced or retracted independently such that the outer delivery catheter 27, pusher catheter 23 and anchor 25, the inner guiding catheter 28 and the needle 21 can be moved relative to the other. This movement is typically performed from the proximal end of the delivery device by a handle that has controls for each part of the device. In the above preferred embodiment, the needle 21 is housed in a protective guide catheter 28 which among other things, serves to protect the instrumentation channel of an endoscope or other such device from damage by the sharp needle tip 42. The guide catheter 28 also provides support, or column strength augmenting penetration force as the delivery needle 21 is advanced. The delivery needle can be advanced in the distal direction outside of the delivery device and conversely the outer sheath 27 can be manually advanced to cover the length of the needle 21.

Figure 5:
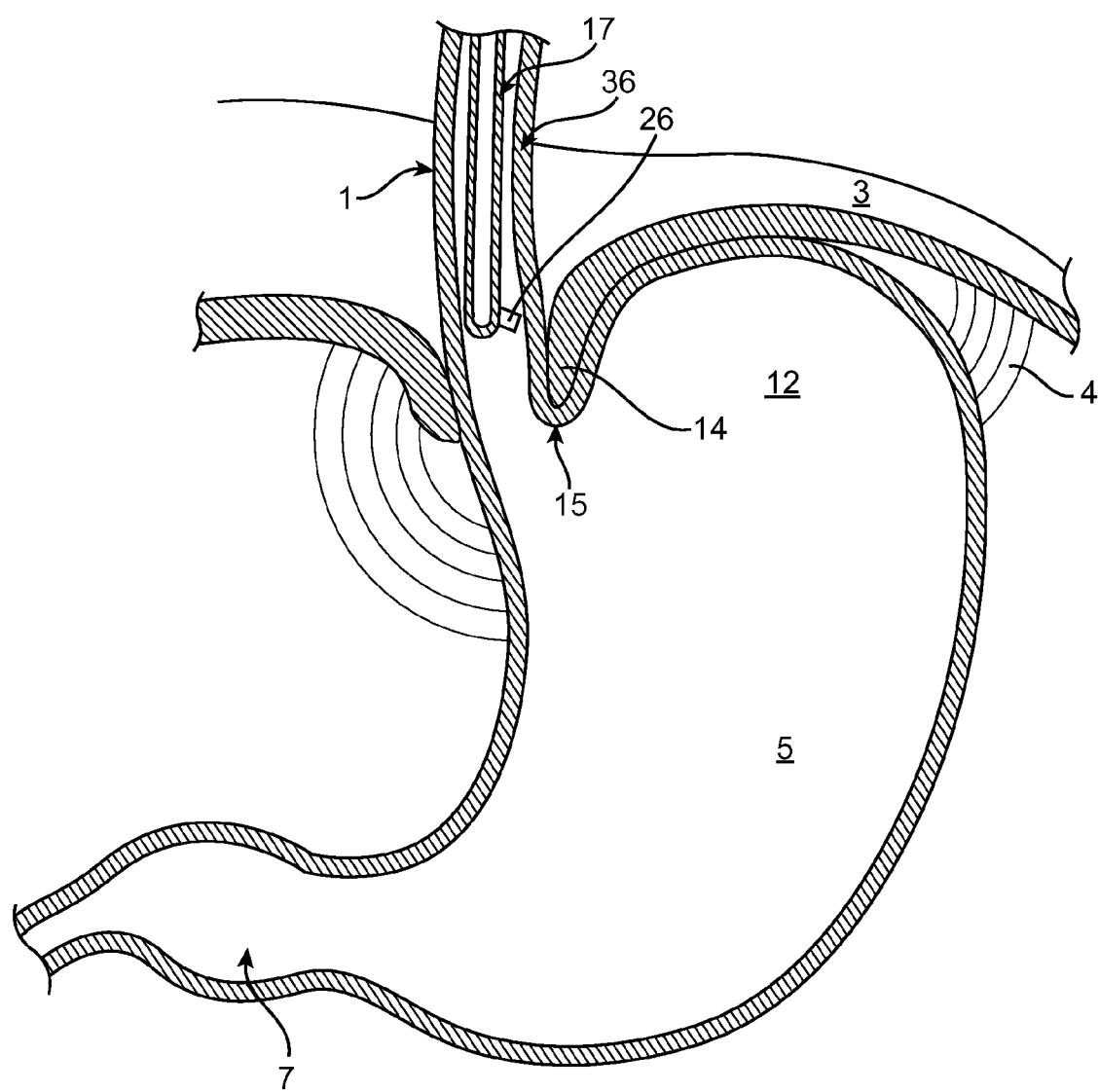
FIG. 5 is a cross sectional view of the gastrointestinal tract in the area of the gastroesophageal junction (GEJ) illustrating the initial advancement of the delivery device.

In a preferred method of the present invention, FIG. 5 shows an EUS endoscope 17 positioned in the patient's esophagus 1 to a position near or adjacent to the LES. Although a non-EUS endoscope may be used, an EUS endoscope is preferred so that structures both inside and outside the walls of the esophagus can be visualized. When the EUS endoscope 17 is properly positioned, the working channel is directed toward the inner wall of the esophagus 1 (i.e. toward the fundus 12) and the delivery device 26 is advanced out of the endoscope working channel so that it protrudes by about 0.5 cm to 3 cm, and most often about 1 cm. This distance is not critical and only allows the catheter device 29 to clear the end of the working channel and to avoid damage to the device from the endoscope elevator, if present. The needle 21 pierces the esophageal wall 36 and is then directed under ultrasonic guidance through the diaphragmatic crus 14 and through the wall of the stomach 6 and into fundus 12. It is important that the delivery needle 21 traverses the diaphragmatic crus muscle 14 as this is a fixed structure that will anchor and stabilize the system as opposed to simply attaching to the wall of the stomach and/or esophagus or non-muscular tissue alone.

Figure 6:
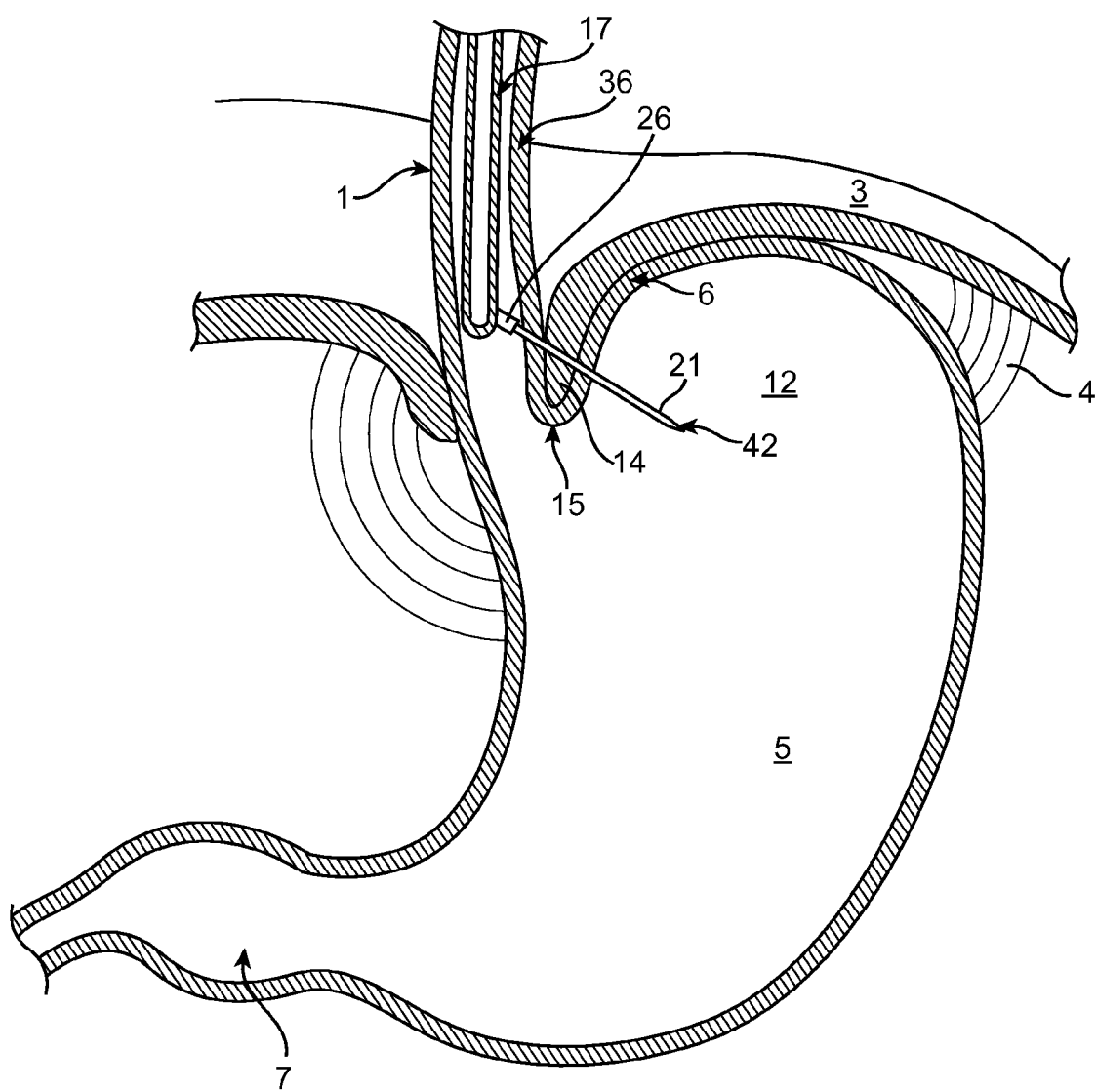
FIG. 6 is a cross sectional view of the gastrointestinal tract in the area of the gastroesophageal junction (GEJ) showing the advanced needle through the crus muscle and other tissues.

Once the distal end of the delivery device 26 is positioned outside of the working channel, needle (or trocar) 21 with sharp tip 42 are pushed or "fired" through the wall of the esophagus 36, the crus 14 and the wall of the stomach 6 into the cavity of the fundus 12 as seen in FIG. 6.

Figure 7:
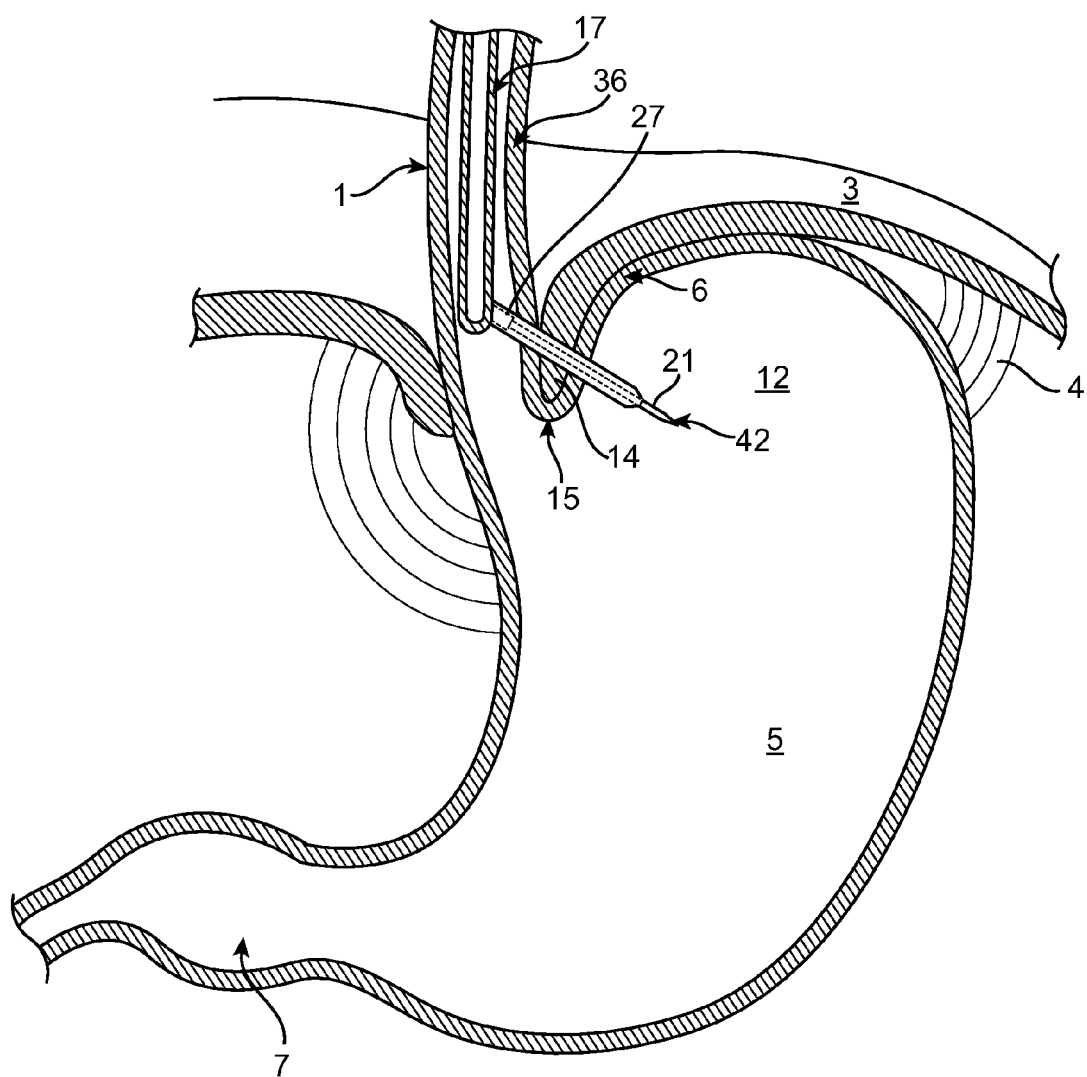
FIG. 7 is a cross sectional view of the gastrointestinal tract in the area of the gastroesophageal junction (GEJ) showing advancement of the delivery catheter over the needle or trocar and through the crus muscle and other tissues.

In FIG. 7, the outer delivery catheter 27 is advanced over the needle 21 through the wall of the esophagus 36, the crus 14, and the wall of the stomach 6, into the cavity of the fundus 12.

Advancement of the delivery catheter can be difficult, due to tissue deflection. A number of methods can be used separately or in combination to stabilize the tissue and advance the catheter. These include but are not limited to: 1) self-tapping threads on the nose cone 46 and distal portion of the outer surface of delivery catheter 27; 2) use of a "T-tag" or the like, deployed through the lumen of the needle 21; 3) a needle or trocar that separates once advanced into the cavity of the fundus; 4) a gradually tapered delivery catheter; and 5) any combination of the above. A threaded nose cone and/or initial segment of the delivery catheter can be advanced through the tissue by clockwise or counter clockwise rotation, depending on the thread direction, to engage the tissue with the threads and draw the catheter into and through the tissue. A T-tag can be fed through the needle and deployed in the fundus to act as an anchor to secure the structure against the advance of the delivery catheter. The needle or trocar can be designed to expand outward, post advancement, preventing motion and securing the structure against the advancement of the delivery catheter. Alternatively a gradually tapered delivery catheter can allow the forward advancement of the delivery catheter through the structure. The esophageal wall itself can also be used as a "back-stop", against which the endoscope can gain a relatively fixed position from which to facilitate needle advancement.

Figure 8:
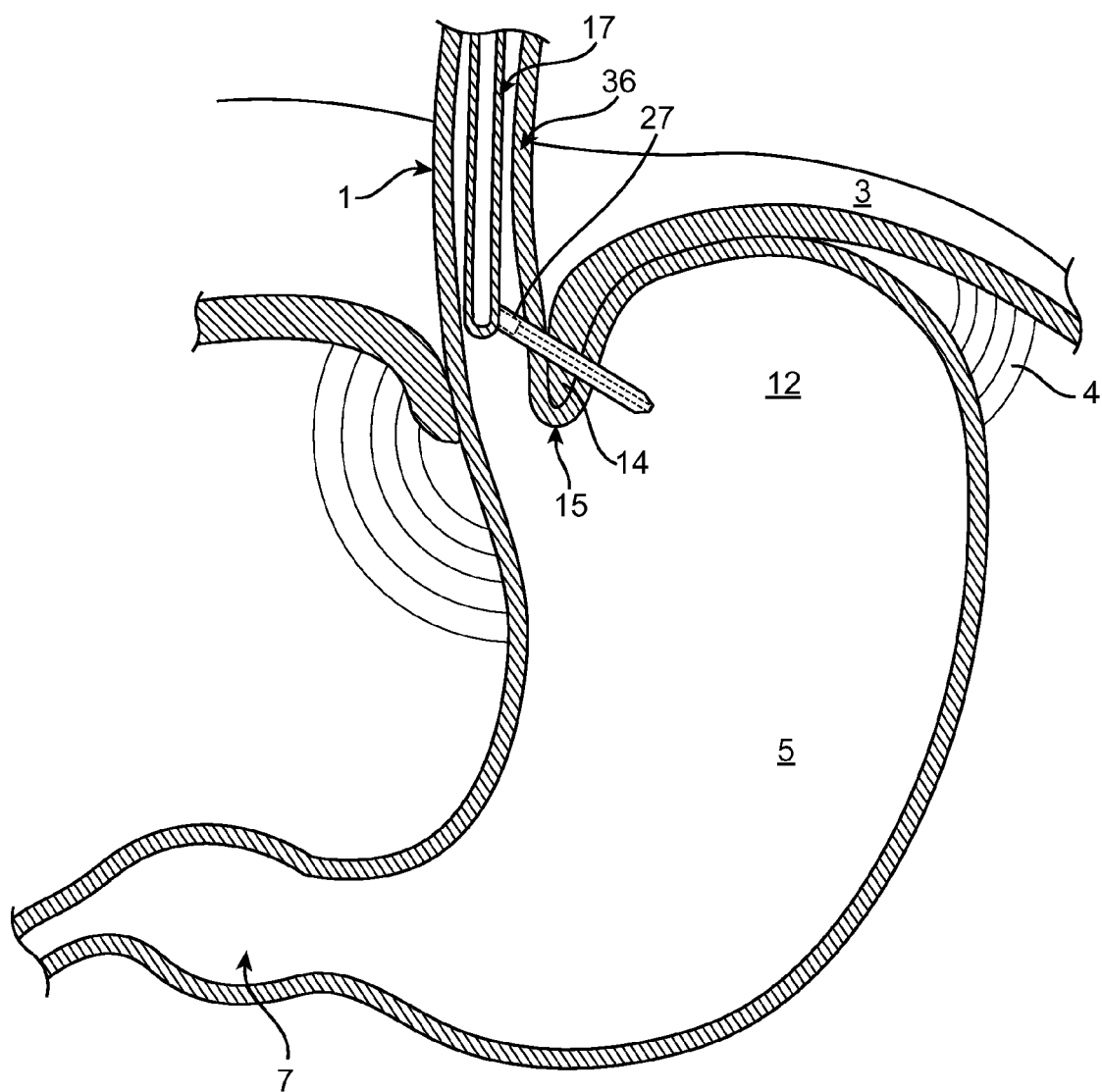
FIG. 8 is a cross sectional view of the gastrointestinal tract in the area of the gastroesophageal junction (GEJ) showing the retraction of the needle.

Following the advancement of the delivery catheter over the needle 21 and into the fundus 12, the needle 21 can be retracted (FIG. 8).

Figure 9:
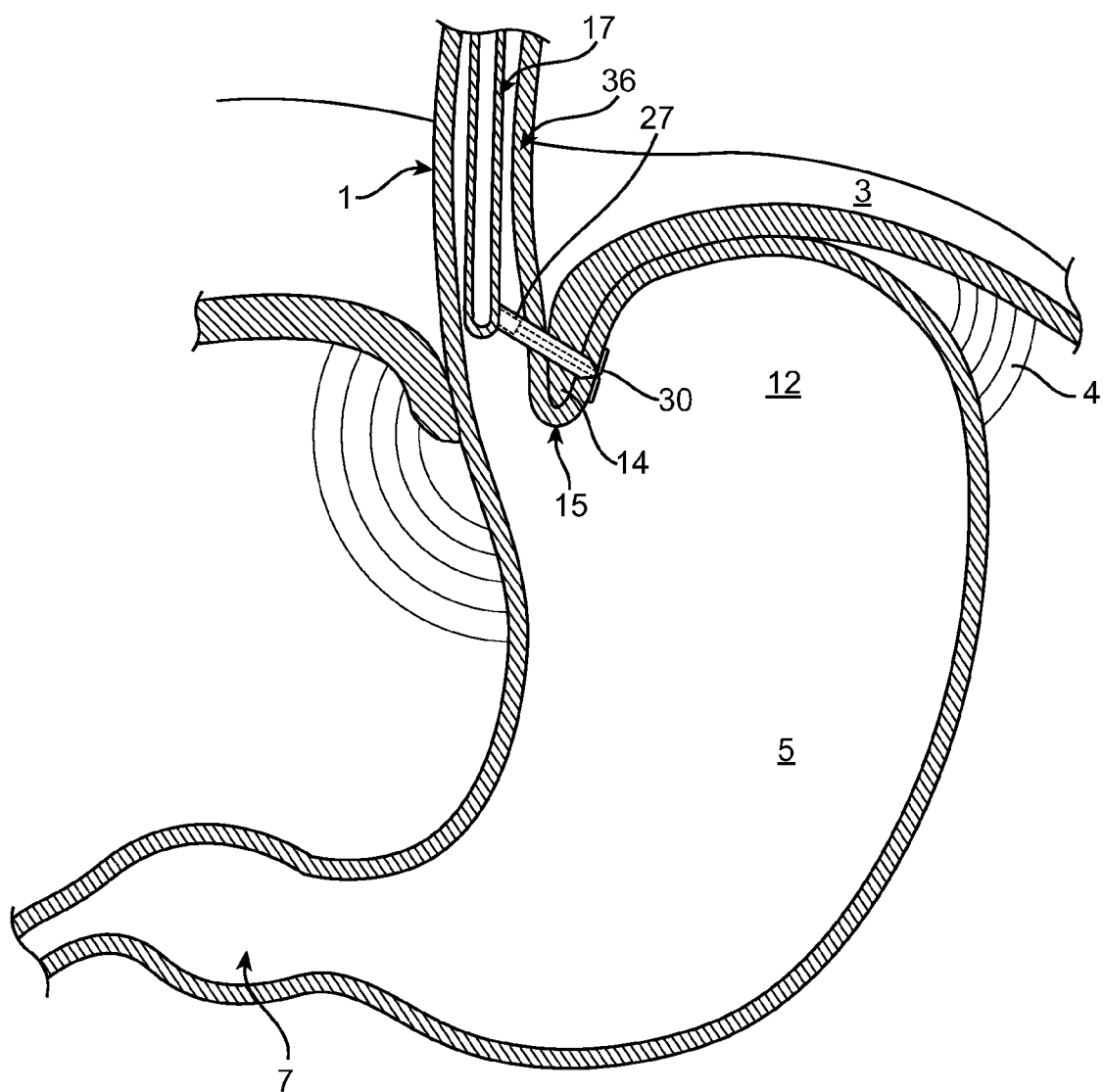
FIG. 9 is a cross sectional view of the gastrointestinal tract in the area of the gastroesophageal junction (GEJ) showing the retraction of the delivery catheter and expansion of the distal anchor.

FIG. 9 shows the retraction of the delivery catheter 27 and expansion of the distal anchor 30 adjacent to the inner wall of the stomach 6.

Figure 10:
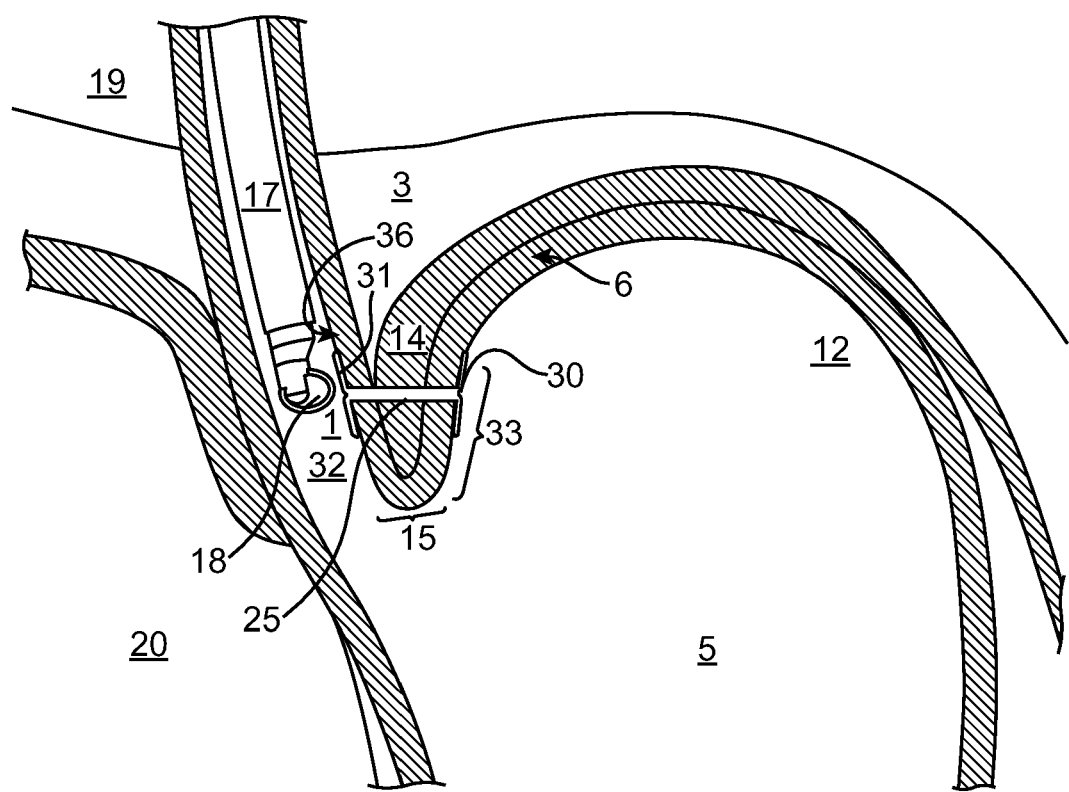
FIG. 10 is a cross sectional view of the gastrointestinal tract in the area of the gastroesophageal junction (GEJ) illustrating the result of treatment where the anchor is holding the fundus to the esophageal wall with the crus muscle therebetween.

FIG. 10 shows the completely retracted delivery catheter and the fully expanded distal 30 and proximal 31 anchors across the esophagus 36, the crus 14 and the wall of the stomach 6. The result of treatment is depicted in FIG. 10: the anchor 25 holds the fundus to the esophageal wall with the crus muscle therebetween providing reduction and stabilization of the hernia. The angle of His 15, the GEV 33 and the LES are properly reconfigured as well.

Successfully capturing the crus muscle with the anchor can be confirmed using the aforementioned visualization or identification methods. Additional anchors may also be deployed as needed to reduce the hernia and re-establish the angle of His.

Deployment of the anchor can be sequential or simultaneous. In a preferred embodiment, the distal anchor is first expanded to hold the anchor in place and prevent it from moving back through the hole while the delivery catheter is retracted allowing the proximal anchor to expand.

Figure 11B:
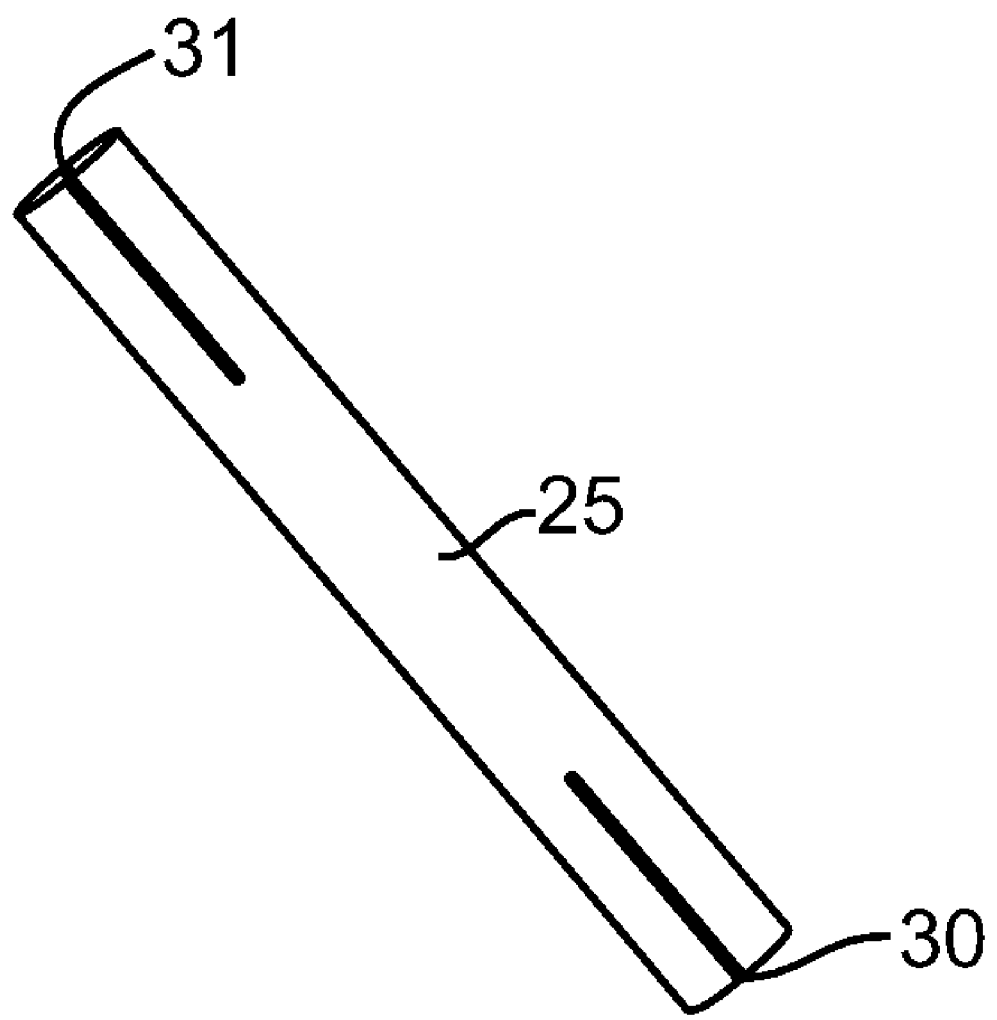
FIG. 11B is a perspective view of the anchor in a constrained configuration.
Figure 11C:
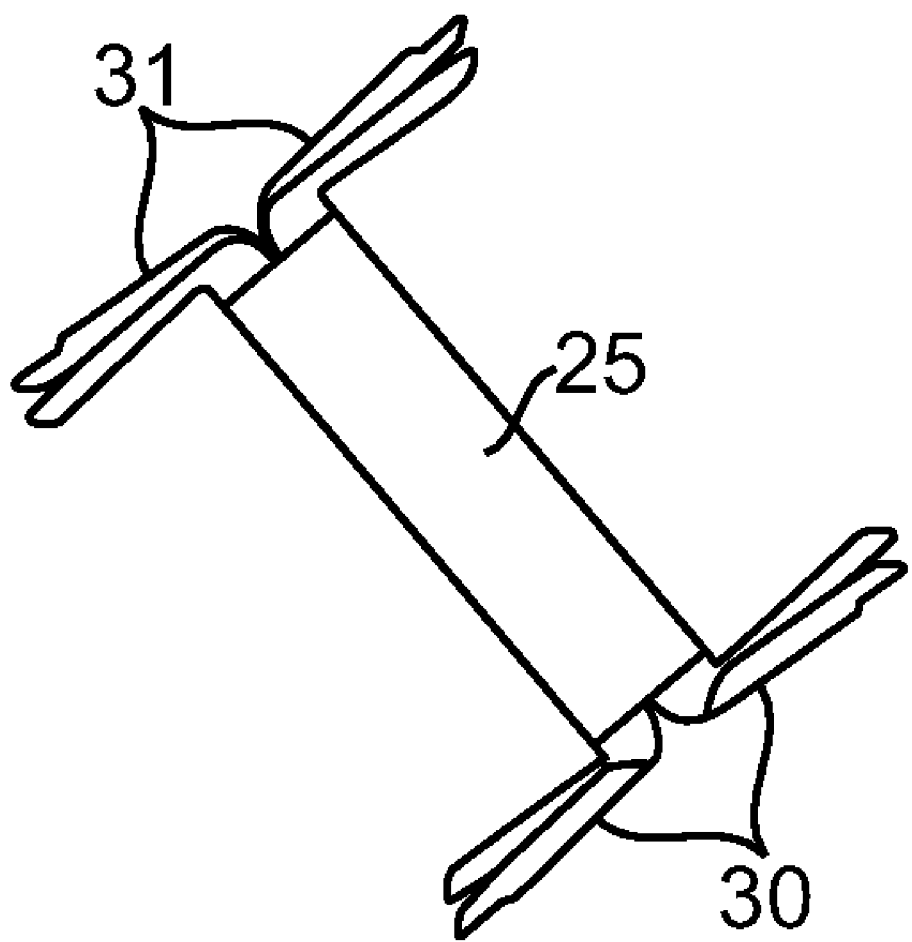
FIG. 11C is a perspective view of the anchor in an expanded configuration.

FIGS. 11B and 11C are exemplary of an anchor of the present invention in the constrained configuration 11B and the expanded configuration 11C. The tissue surfaces are not usually perfectly aligned (i.e. parallel). Preferred anchors will flex and adjust to the anatomy once deployed and are in the expanded configuration.

Figure 11D:
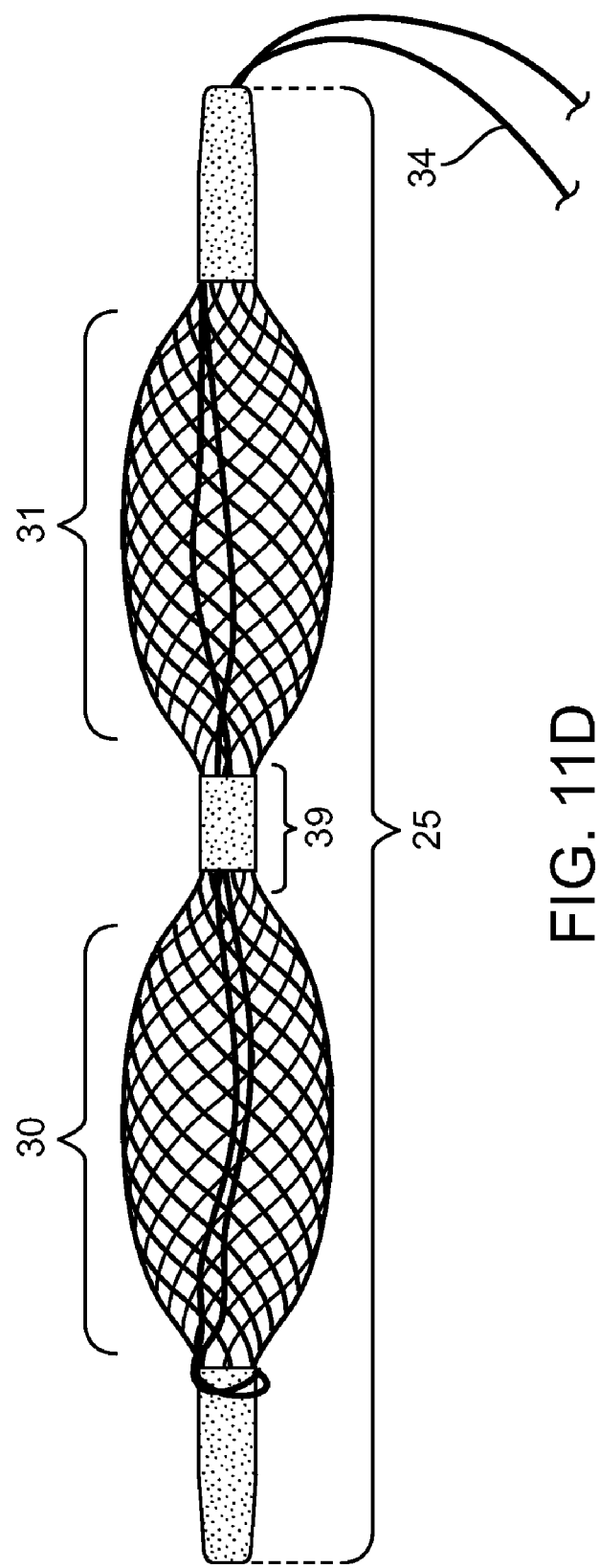
FIG. 11D is a perspective view of a translumenal mesh-type anchor in a constrained or pre-expanded configuration.
Figure 11E:
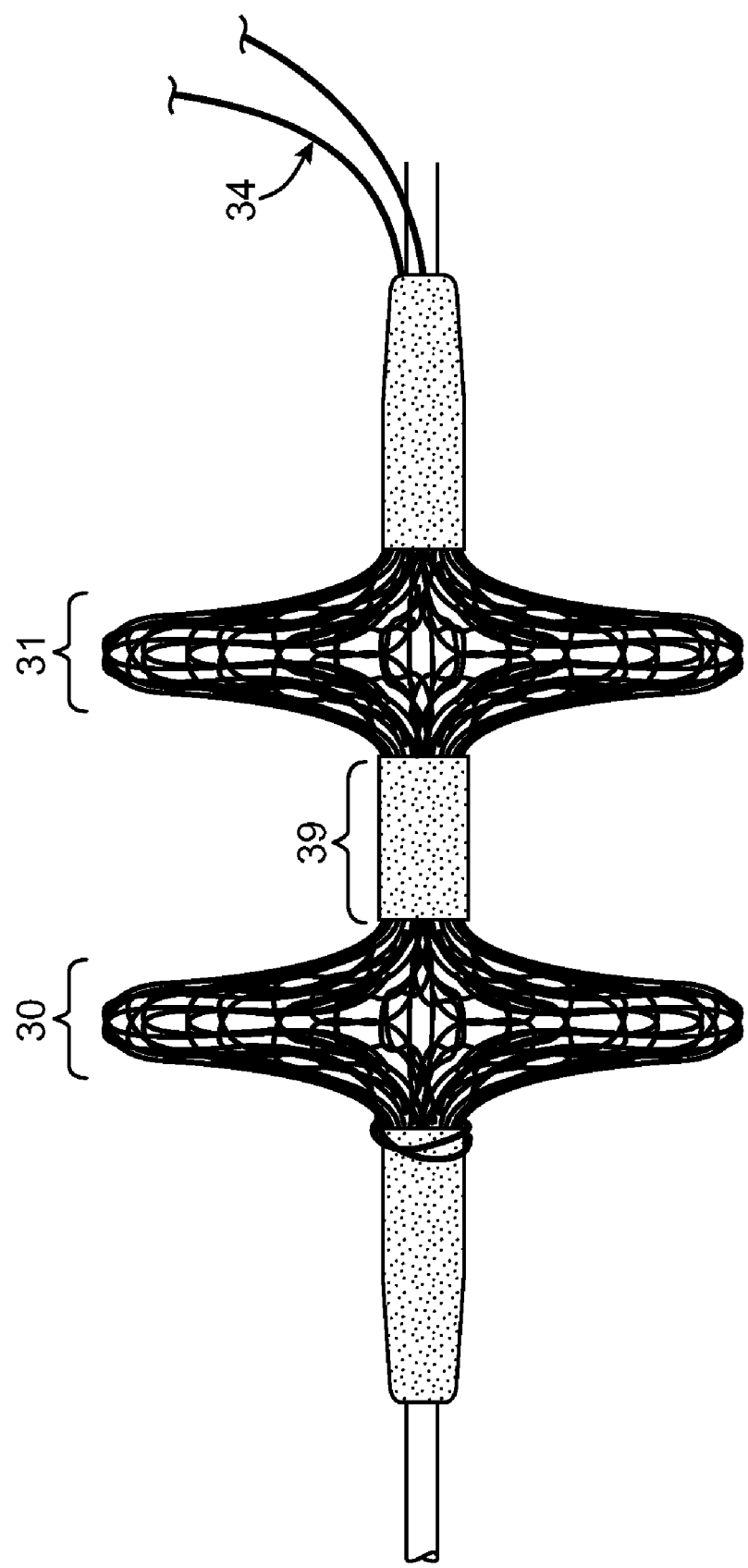
FIG. 11E is a perspective view of a translumenal mesh-type anchor in an expanded or deployed configuration.

In such a preferred embodiment of FIGS. 11D and 11E, one or more drawstrings 34 are attached to the distal end of a mesh-type anchor and pass through the center of the anchor exiting at the proximal end. To deploy the anchor (i.e. expand the ends of the anchor), the health care professional pulls on the drawstring(s) that exit the proximal end, drawing the ends of the anchor together and causing the distal 30 and the proximal 31, ends of the anchor to move from a constrained to an expanded configuration. As shown in FIG. 11E, a predetermined length of anchor shaft 39 retains it's original configuration to accommodate the length of the esophageal wall, crus and stomach tissues that are held together by the expanded anchor. The drawstrings can be tied together, held with a crimping device, or otherwise secured to retain the anchors in their deployed configuration with their ends expanded (FIGS. 10, and 11E). The anchors are designed to permanently remain in place; however, they can also be removed; severing the drawstrings allows the anchor to re-collapse and be removed. This mesh-type anchor can be designed so that the distal and proximal ends can flex and conform to anatomical variation. Various iterations, designs, configurations and types of expandable anchors, including preformed, pre-biased or other suitable anchors for securing tissues are well know in the art and can also be employed using the above-described methods.

The invention has been described and specific examples of the invention have been portrayed. The use of those specific examples are not intended to limit the invention in any way. Additionally, to the extent that there are variations of the invention, which are within the spirit of the disclosure or equivalent to the inventions found in the claims, it is intended that this disclosure will cover those variations as well. While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating a hiatal hernia which extends into a patient's esophagus and restoring a GEV and the angle of His, said method comprising:
   moving the hiatal hernia downwardly to capture a crus muscle between a lower esophageal wall and a gastric fundus;
   visually confirming that the crus muscle is located between the lower esophageal wall and the gastric fundus at a target site; and
   fastening at least the lower esophageal wall to the gastric fundus with a fastener that passes through the crus muscle at a target site to restore the GEV and the angle of His.

2. A method as in claim 1, wherein moving the hiatal hernia comprises:
   advancing an instrument down the esophagus;
   engaging the end of the instrument against the herniated portion of the esophageal wall; and;
   repositioning the hernia toward the stomach.

3. A method of claim 1, wherein visually confirming comprises ultrasonic imaging.

4. A method as in claim 1, wherein fastening comprises:
   deploying a delivery device; and
   advancing the fastener through the delivery device.

5. A method as in claim 4, wherein the fastener comprises a central portion having two expandable end anchors which expand and engage the esophagus and fundus, respectively.

6. A method for restoring a GEV and the angle of His, said method comprising:
   positioning an instrument in the esophagus;
   visually confirming a crus muscle is captured between the lower esophageal wall and the gastric fundus at a target site; and
   fastening the lower esophageal wall to the gastric fundus with a fastener that passes through the diaphragmatic crus muscle at the target site to restore the GEV and the angle of His.

7. A method of claim 6, wherein fastening comprises advancing the fastener through a delivery device.

8. A method of claim 6, wherein the fastener is passed from the thoracic cavity to the abdominal cavity.

9. A method of claim 6, wherein the fastening restores the gastro-esophageal flap valve.

10. A method of claim 6, wherein the fastening repositions the lower esophageal sphincter against the diaphragmatic crus muscle.

11. A method of claim 6, wherein the fastening enhances the function of the lower esophageal sphincter.

12. A method of claim 6, wherein the fastening restores the anti-reflux barrier.

13. A method of claim 6, wherein the angle of His is restored by treating a hiatal hernia.

14. A method for treating a hiatal hernia and restoring a GEV and the angle of His, said method comprising:
   visually identifying a target site through the lower esophageal wall and the gastric fundus where the crus muscle is positioned therebetween; and
   fastening the lower esophageal wall to the gastric fundus with a fastener that passes through the diaphragmatic crus muscle to restore the GEV and the angle of His.

15. A method of claim 14, wherein the hiatal hernia is first repositioned downwardly to capture the crus muscle at the angle of His.

16. A method of claim 14, that results in reducing the hernia.

17. A method of claim 15, wherein pushing the hiatal hernia comprises engaging the hernia with the expanded cuff of the endoscope and pushing the hernia downward.

18. A method of claim 14, wherein the hiatal hernia can be pushed or pulled down by mechanical pushers or pullers, vacuum apparatus, inflatable members, pins, traction devices or the like, either associated with an endoscope or as separate devices.

19. A method of claim 14, wherein fastening comprises advancing the fastener through the endoscope.

20. A method of claim 14, wherein the fastening comprises delivery of the fastener using a catheter.

21. A method of claim 14, wherein the fastener is passed from the thoracic cavity to the abdominal cavity.

22. A method of claim 14, wherein the fastening restores the gastro-esophageal flap valve.

23. A method of claim 14, wherein the fastening repositions the lower esophageal sphincter against the diaphragmatic crus muscle.

24. A method of claim 14 wherein the fastening enhances the function of the lower esophageal sphincter.

25. A method of claim 14 wherein the fastening restores the anti-reflux barrier.

26. A method of claim 14 wherein the angle of His is restored by treating a hiatal hernia.

27. A method of claim 6 or claim 14 wherein the fastener comprises a central portion having two expandable end anchors which expand and engage the esophagus and gastric fundus, respectively.

28. A method of claim 6 or claim 14 wherein the fastener is removable.

29. A method of claim 1 or claim 14 wherein the fastening occurs in the direction from the esophagus toward the fundus.

30. A method of claim 1 or claim 14 wherein the fastening occurs in the direction from the fundus toward the esophagus.

* * * * *